US012727922B2

(12) United States Patent
Hill

(10) Patent No.: US 12,727,922 B2
(45) Date of Patent: Sep. 8, 2026

(54) TEMPORARILY FLEXIBLE IMPLANTABLE ROD PLACEMENT AND FABRICATION

(71) Applicant: WONDERHEALTH LLC, Atlanta, GA (US)

(72) Inventor: Kenneth Hill, Jacksonville, FL (US)

(73) Assignee: WONDERHEALTH LLC, Atlanta, GA (US)

( * ) Notice: Subject to any disclaimer, the term of this patent is extended or adjusted under 35 U.S.C. 154(b) by 815 days.

(21) Appl. No.: 17/819,823

(22) Filed: Aug. 15, 2022

(65) Prior Publication Data

US 2022/0387079 A1 Dec. 8, 2022

Related U.S. Application Data

(63) Continuation of application No. 17/046,093, filed as application No. PCT/US2019/026951 on Apr. 11, 2019, now Pat. No. 11,413,071.

(60) Provisional application No. 62/655,855, filed on Apr. 11, 2018.

(51) Int. Cl.
*A61B 17/70* (2006.01)
*A61L 27/18* (2006.01)

(52) U.S. Cl.
CPC ...... *A61B 17/7031* (2013.01); *A61B 17/7032* (2013.01); *A61L 27/18* (2013.01)

(58) Field of Classification Search
CPC .. A61B 17/7002; A61B 17/7026–7031; A61B 17/7011–7013
See application file for complete search history.

(56) References Cited

U.S. PATENT DOCUMENTS

| | | | | |
|---|---|---|---|---|
| 5,658,286 A * | 8/1997 | Sava | A61B 17/7013 606/279 |
| 8,529,602 B2 | 9/2013 | Richelsoph | |
| 11,413,071 B2 * | 8/2022 | Hill | A61B 17/7019 |
| 2005/0277934 A1 * | 12/2005 | Vardiman | A61B 17/7083 606/915 |
| 2007/0191845 A1 | 8/2007 | Justis | |

(Continued)

OTHER PUBLICATIONS

Extended European Search Report dated Dec. 9, 2021 (Copy filed in parent application).

(Continued)

*Primary Examiner* — Eduardo C Robert
*Assistant Examiner* — Michelle C Green
(74) *Attorney, Agent, or Firm* — Perilla Knox & Hildebrandt LLP; James J. Rha

(57) ABSTRACT

Disclosed are various embodiments for forming spinal rod members for use in pedicle screw systems for spinal fixation surgery and systems. A system can include a pedicle screw having a pedicle screw head and a pedicle screw shaft, the pedicle screw head comprising an aperture for receiving and retaining a spinal rod member relative to the pedicle screw. The spinal rod member can include an elongated tubular membrane having a flexible body and a spinal rod body formed of a compound, where the spinal rod body is formed by insertion of a liquid compound into the elongated tubular membrane and a hardening of the liquid compound or other similar process for conversion of the flexible rod to a rigid rod. The pedicle screw head can include a channel configured to receive and retain the spinal rod member.

19 Claims, 3 Drawing Sheets

(56) References Cited

U.S. PATENT DOCUMENTS

| | | | | |
|---|---|---|---|---|
| 2007/0191846 | A1* | 8/2007 | Bruneau | A61B 17/7008 606/86 A |
| 2007/0270953 | A1* | 11/2007 | Trieu | A61F 2/442 623/17.11 |
| 2008/0086126 | A1 | 4/2008 | Miller | |
| 2008/0125777 | A1* | 5/2008 | Veldman | A61B 17/7029 606/103 |
| 2008/0154367 | A1* | 6/2008 | Justis | A61B 17/7013 606/76 |
| 2009/0112265 | A1* | 4/2009 | Hudgins | A61B 17/7031 606/301 |
| 2010/0121380 | A1 | 5/2010 | Justis et al. | |
| 2011/0054480 | A1 | 3/2011 | Rabiner et al. | |

OTHER PUBLICATIONS

International Search Report and Written Opinion for PCT/US2019/026951 mailed Aug. 7, 2019 (Copy filed in parent application).

International Preliminary Report on Patentability for PCT/US2019/026951 mailed May 2, 2020 (Copy filed in parent application).

* cited by examiner

TEMPORARILY FLEXIBLE IMPLANTABLE ROD PLACEMENT AND FABRICATION

CROSS-REFERENCE TO RELATED APPLICATION

This application is a continuation of U.S. patent application Ser. No. 17/046,093 filed Oct. 8, 2020, which is a 35 U.S.C. § 371 national phase application of International Application No. PCT/US2019/026951 entitled "TEMPORARILY FLEXIBLE IMPLANTABLE ROD PLACEMENT AND FABRICATION," filed Apr. 11, 2019, which claims the benefit of and priority to U.S. Provisional Patent Application No. 62/655,855 entitled "TEMPORARILY FLEXIBLE IMPLANTABLE ROD PLACEMENT AND FABRICATION," filed Apr. 11, 2018, the contents of all of which being incorporated by reference in their entireties herein.

BACKGROUND

Surgical screw-based rod instrumentation in specialty surgery, i.e. pedicle screws, are surgically implanted medical devices that include, but are not limited to, a specialized screw commonly used in spine surgery for the stabilization of spinal sections. This intervention is commonly performed to produce spinal stability for neuronal function preservation, pain relief, deformity correction, etc. In conventional spinal instrumentation, the screw and rod construction is composed of multiple components which generally includes a screw head, a closure cap, a screw shaft, and a spinal rod which is used to connect two or more screws together in a segmental or non-segmental series.

The metal alloy composition of the spinal rod is usually stainless steel, titanium, cobalt chromium or other, though other compounds with less rigid composition have also been developed. Internal anatomy and pathophysiology differs widely and no two individuals requiring surgery have uniform spinal alignment. Additionally, intentional correction of undesired spinal alignment requires the development of a personalized rod structure. Additional surgery, during which connection of a construct with a previously implanted construct, requires real-time adjustments of implanted metal. Lastly, there are also changing variables to rod alignment based on the surgical technique and comfort level of the operating surgeon.

As such, during surgery the spinal rod must be adjusted and bent from predetermined shape of straight or nearly straight to form the appropriate curvature for engaging the already placed screw constructs, i.e. pedicle screw, that also corresponds with the larger alignment of concavity and convexity desired for the spinal column. This process requires a traditional manual manipulation of the rod or repositioning of implanted screws. This is labor intensive, and bending the spinal rod can be mentally difficult. Attempting to recapitulate the three dimensional contour required for implantation is done in a separated environment (over the patient or on the back table). This is labor intensive and it can also significantly increase surgery times. This process requires a great degree of trial-and-error until the curvature of the spinal rod is matched the internal or desired internal alignment. Of note, a similar process can be required in a number of additional surgical specialties, as this specifically speaks to spinal fixation.

FIELD OF THE INVENTION

The present invention relates generally to spinal fixation devices for the internal fixation of the spine, particularly within the fields of neurosurgery, orthopedics, and other fields associated with spinal alignment procedures and spinal implants that include pedicle screws, lateral mass screws, anterior, lateral, oblique spinal screws, occipital, sacral and pelvic fixation and spinal rods for fixing, correcting and retaining vertebral bones relative to one another.

BRIEF SUMMARY OF THE INVENTION

Various embodiments are disclosed for forming spinal rod members for use in pedicle screws; lateral mass screws; trans-articular screws; cortical screws; laminar screws; facet screws; anterior, lateral and oblique screws; occipital, sacral and pelvic fixation screws (from now on generally referred to as a "pedicle screw") for spinal instrumentation and fixation surgery and systems. A particular pedicle screw system can include a pedicle screw having a pedicle screw head and a pedicle screw shaft, the pedicle screw head being configured to receive and retain a spinal rod member relative to the pedicle screw. The spinal rod member can include a predetermined rigid rod configuration, an elongated tubular membrane having a flexible body and a spinal rod body formed of a compound, where the spinal rod body is formed by insertion of a liquid compound into the elongated tubular membrane and a hardening of the liquid compound. The pedicle screw head can include a channel or an aperture configured to receive and retain the spinal rod member relative to the pedicle screw and relative to bone.

Further, a method can include attaching a first pedicle screw to a first vertebrae of a spine and attaching a second pedicle screw to a second vertebrae of the spine, where the first pedicle screw and the second pedicle screw each include a pedicle screw head and a pedicle screw shaft. The pedicle screw head can be configured to retain a spinal rod member relative to the first pedicle screw and the second pedicle screw. Further, the method can include forming the spinal rod member by positioning a flexible and elongated tubular membrane that will maintain a competent inner channel into the pedicle screw head of the first pedicle screw and the second pedicle screw, inserting a liquid compound into the elongated tubular membrane, hardening the liquid compound to form a hardened spinal rod member body. Additional embodiments can include forming the spinal rod member by positioning a multi-segmented flexible and elongated rod to the pedicle screw head of the first pedicle screw and the second screw that after capturing the rod within the pedicle screw head will then made rigid by a collapsing of the segments to a rigid construct. Additional embodiments would include yet to be developed easily influenced liquids, semi-solid or solid compounds that can be converted into a rigid state in a fashion that can be implanted for the purposes of spinal instrumentation and fixation

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1:
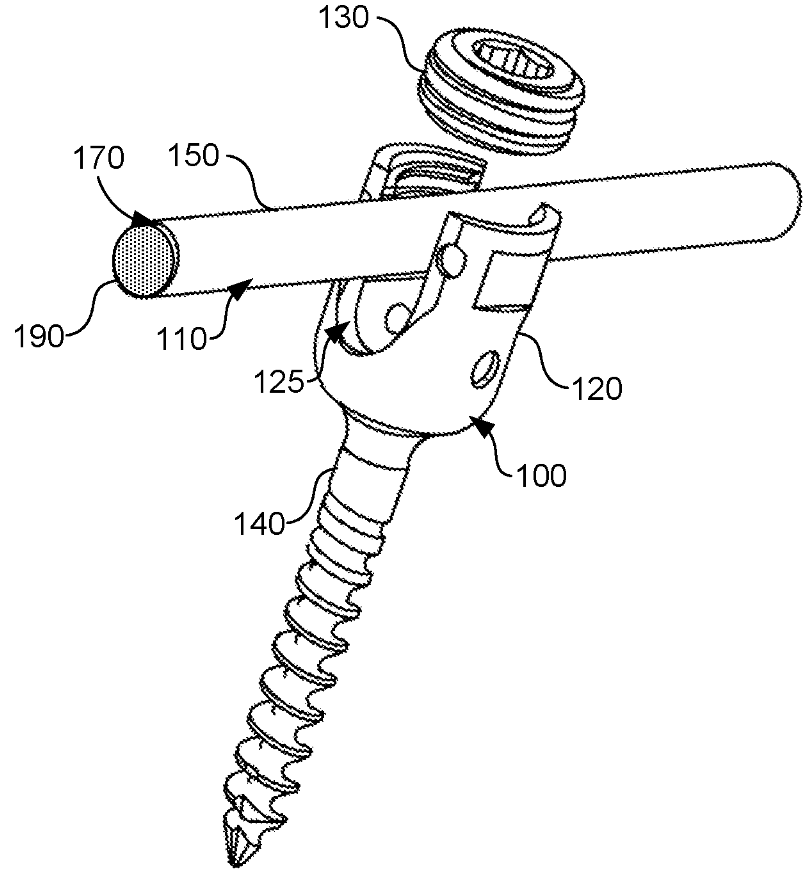
FIG. 1 shows an example of a pedicle screw having a spinal rod member according to various embodiments of the present disclosure.

The present disclosure relates to a pedicle screw spinal rod placement system that includes a temporarily flexible member and a method of fabricating the same. A pedicle screw as outlined in this disclosure represents a number of screw fixation techniques utilized in the fixation and stabilization of the spinal columns and includes open, percutaneous, minimally invasive and other surgical techniques. Other similar screw types used for stabilization that are also represented within the identification of "pedicle screw" include, but are not limited to, lateral mass screw; transarticular screw; cortical screw; laminar screw; facet screw; anterior, lateral and oblique screw; and occipital, sacral and pelvic fixation, though the specifics of screw differentiation will not be discussed here.

As noted above, pedicle screws are medically implanted surgical devices that include a specialized screw commonly used in surgery for the stabilization of spinal sections to create spinal stability, correct pathologic spinal alignment, achieve preservation or improvement of neuronal or other medically dependent function, and/or to relieve or alleviate pain. In conventional screw fixation, the screw is composed of multiple basic components generally including, but not limited to, a screw head which can be in a fixed orientation to polyaxial in nature, a closure cap or entrapment construct to house the spinal rod construct, a shaft with a variety in pitch for thread development, and a spinal rod which is used to connect two or more screws together in a non-segmental or segmental series. The spinal rod characteristics typically represent an elongated rod implant that is cylinder in shape and can be of various lengths, though other embodiments include a less circular shape, plating type system or other type devices used to connect vertebral segments. The spinal rod is usually composed of a type of stainless steel, including but not limited to, titanium or cobalt chromium, though additional less or more rigid rod composition is sometimes employed.

Historically, certain systems used for spinal fixation have been referred to as a Harrington rod. As such, during surgery the spinal rod must be adjusted and bent from a predetermined shape of straight or nearly straight to form the appropriate curvature for engaging the already placed screw constructs, i.e. pedicle screw, that also corresponds with the larger alignment of concavity and convexity desired of the spinal column. This alignment can be determined to maintain a currently determined alignment based on a patient's pathophysiology or to correct the alignment with subsequent fixation for healing to achieve a desired radiographic and clinical outcome.

The process of spinal rod adjustment traditionally requires a manual manipulation of the rod or repositioning of implanted screws. Manually adjusting and bending of the spinal rod can be mentally difficult to recapitulate the three-dimensional contour required for internal implantation, as this process of manual bending traditionally is completed in a separate environment (over the patient or on the back table) and is labor intensive. In situ spinal rod bending is also difficult and potentially hazardous as large amounts of force are required with instruments that can be difficult to get into the surgical site. Spinal rod bending can significantly increase surgery times. This process requires a great degree of trial-and-error until the curvature of the spinal rod can match the implanted and desired internal anatomy. In addition, a similar process of trial-and-error can be required in a number of other surgical procedures for implantation of a rigid construct to allow for correction and stabilization of physiologic structures though this document specifically speaks to spinal fixation.

Accordingly, various embodiments are disclosed regarding the forming of spinal rod members for use in pedicle screw systems during spinal fixation surgery. In addition, various embodiments are disclosed regarding the systems that require improved techniques for adjusting and do not require manual bending of stainless steel metal spinal rods or other members. A system can include a pedicle screw having a pedicle screw head and a pedicle screw shaft, where the pedicle screw head is configured to receive and retain a spinal rod member relative to the pedicle screw. The spinal rod member can include an elongated tubular membrane having a flexible body and a spinal rod body formed of a single element or compound, including but not limited to a derivative of a plastic compound, primary element, metal alloy, other compound or other, where the spinal rod body is formed by insertion of a liquid compound into the elongated tubular membrane and a hardening of the liquid compound.

The hardening process of the liquid compound can comprise a number of potential methods. Methods can include, but are not necessarily limited to, waiting a predetermined amount of time, an application of an additional agent that invokes a chemical reaction to harden the liquid compound, photo or electrical curation, a multistep process of hardening, metal alloy selection that has intrinsic properties for hardening, use of other element or compound that has innate or adjustable properties that can be manipulated or adjusted in a controlled fashion to convert from a first state that can easily be maneuvered to a more rigid state, temperature curing methods, a combination thereof, or other currently established or future developed procedures for conversion of a malleable/flexible rod to a rigid structure whether this process is completed within the surgical wound or outside the surgical wound for implantation. The tensile and fatigue strength of the spinal rod can be variable and can depend on the desired rigidity of the rod based on previous surgery, the surgical expectations by the surgical team and long-term goals of the construct. The pedicle screw head can include a channel configured to receive and retain the spinal rod member, as can be appreciated.

Further, a method can include attaching a first pedicle screw to a first vertebrae of a spine and attaching a second pedicle screw to a second vertebrae of the spine, where the first pedicle screw and the second pedicle screw each include a pedicle screw head and a pedicle screw shaft that can be cannulated, pores or not. The rigid or polyaxial pedicle screw head can be configured to retain a spinal rod member relative to the first pedicle screw and the second pedicle screw. Further, the method can include forming the spinal rod member by positioning a flexible and elongated tubular membrane into the pedicle screw head of the first pedicle screw and the second pedicle screw, inserting a liquid compound into the elongated tubular membrane, hardening the liquid compound to form a hardened spinal rod member body. Additional embodiments can include forming the spinal rod member by positioning a multi-segmented flexible and elongated rod to the pedicle screw head of the first pedicle screw and the second screw that after capturing the rod within the pedicle screw head will then be made rigid by a collapsing of the segments to a rigid construct. Additional embodiments can further include yet to be developed easily influenced liquids, semi-solid, or solid compounds that can be converted into a rigid state in a fashion that can be implanted for the purposes of spinal instrumentation and fixation.

Turning now to FIG. 1, a non-limiting example of a pedicle screw 100 and a spinal rod member 110 is shown according to various embodiments. The pedicle screw 100 and the spinal rod member 110 can be used as a component in a spinal rod type spine fixation system or assembly, as will be appreciated.

More specifically, the pedicle screw 100, similar screw implant, or other similar apparatus can be employed to attach or fix a section of the spinal rod member 110 or similar rod construct, plating system, or other similar system relative to a vertebrae or section of vertebra of the spine with or without fixation to the skull base, sacrum and/or pelvis (not shown). More specifically, the pedicle screw 100 is configured to be attached to a vertebra in a manner known in the art by skilled surgeons or other medical practitioners, while a pedicle screw head 120 of the pedicle screw 100 comprises a pedicle screw aperture 125 that receives, fixes, retains, and holds a section of the spinal rod member 110 therein. It is understood that the vertebra can include vertebra of a mammal, such as a human, dog, cat, horse, or other mammal. In some embodiments, the pedicle screw head 120 can be movable and repositioned relative to the pedicle screw 100.

Further, in some embodiments, the pedicle screw head 120 includes a coupling element 130 that is detachable and can be attached to the pedicle screw head 120, for instance, to capture and retain the spinal rod member 110 or similar rod construct, plating system or other to the pedicle screw 100. The pedicle screw head 120 can be attached to a pedicle screw shaft 140, which can include threaded elements (i.e., male threaded elements) for insertion into bone, such as vertebrae or other spinal segmental anatomical locations of a spinal column or other suitable bone structure.

As noted above, conventional spinal rod implants or Harrington rods including screws, rods, hooks and connectors are composed of stainless steel or other type of metal or high tensile strength materials. Implant construct testing includes the fatigue strength of the construct over time. As such, during surgery, the spinal rod must be adjusted and bent from a predetermined shape of straight or nearly straight to form the appropriate curvature for engaging the already placed screw constructs (e.g., a pedicle screw) that also corresponds with the larger alignment of concavity and convexity desired of the spinal column.

The alignment can be determined to maintain a desired alignment based on a patient's pathophysiology or to correct the alignment with subsequent fixation for healing to achieve a desired radiographic and clinical outcome. This commonly requires bending of a particular rod in multiple three-dimensional directions for proper implantation. The process of spinal rod adjustment traditionally requires a manual manipulation of the rod or repositioning of implanted screws. Manually adjusting and bending of the spinal rod can be mentally difficult to recapitulate the three-dimensional contour required for internal implantation as this process of manual bending traditionally is completed in a separate environment (over the patient or on a back table in an operating room) and is labor intensive. Spinal rod bending can significantly increase surgery times. This process requires a great degree of trial-and-error until the three-dimensional curvature of the spinal rod can match the implanted and desired internal anatomy. As such, according to various embodiments of the present disclosure, a spinal rod member 110 can be formed, for instance, during a surgery on a spinal column or other portion of the body without having to bend stainless steel or other material.

In various embodiments, the spinal rod member 110 can include an elongated tubular membrane 150 having a flexible body. In some embodiments, the elongated tubular member 150 can be formed of plastic, other semi-solid, malleable solid or other suitable material. The flexible body can be used, for instance, to position the elongated tubular membrane 150 in the screw head aperture 125 (or other receptacles of channels) of one or more screw heads 120. In some embodiments, after the elongated tubular member 150 is positioned in the channels 160, the coupling element 130 or other functionally similar coupling element can be used to secure the elongated tubular membrane 150 to the pedicle screws 100. The elongated tubular membrane 150 can include a hollow interior 170 in some embodiments. As such, the elongated tubular member 150 can be formed of a material that provides some structural resistance when the coupling element 130 is attached, such that a body of the spinal rod member 110 to be formed includes a substantially uniform or a uniformity that is not statistically and/or functionally significantly different in cross-section across all portions of the spinal rod member 110. The spinal rod member 110 can include a substantially straight shape or a curvilinear shape, as shown in FIG. 2.

Figure 2:
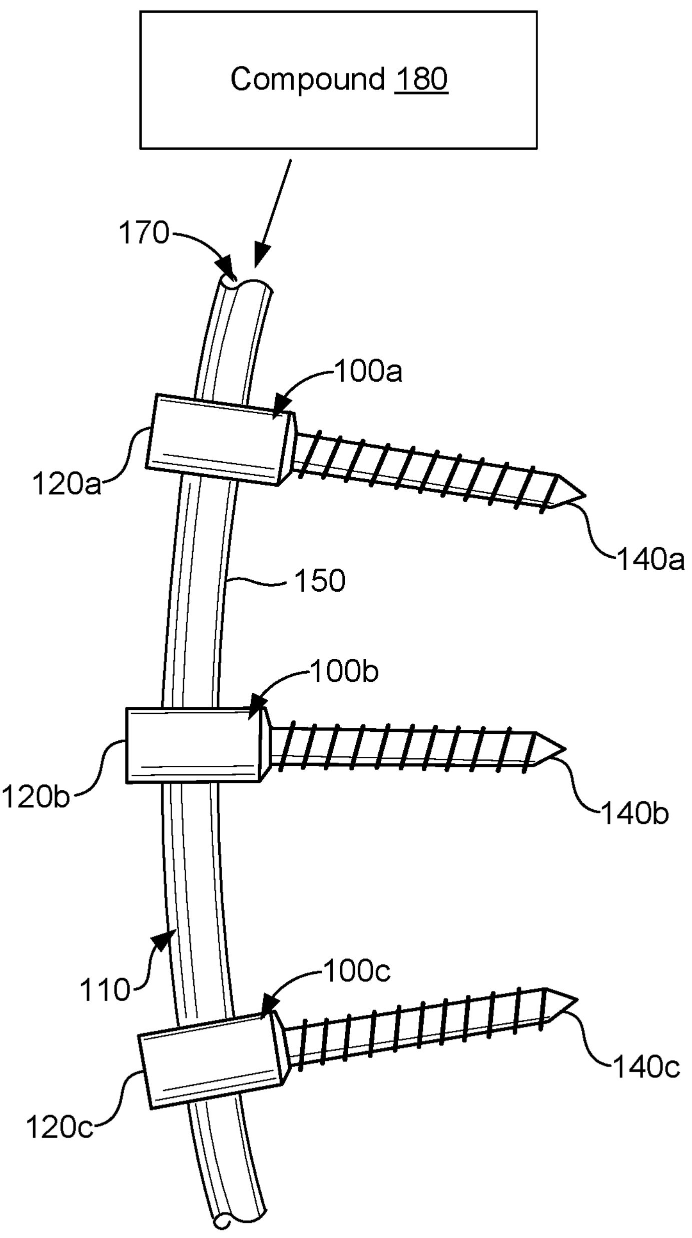
FIG. 2 shows an example of multiple pedicle screws having a spinal rod member forming a curvature according to various embodiments of the present disclosure.

In one embodiment the hollow interior 170 of the elongated tubular membrane 150 can be filled by insertion of a compound 180, as shown in FIG. 2, such as a liquid or semisolid compound, thereby forming a spinal rod body 190 when the compound has settled and hardened. The method for hardening can be one of a number of different controlled properties of the initial compound or an activation of the liquid or semi-solid compound by any of a number of external factors. The extent of potential external factors are not limited within this description. Further, as shown in FIG. 2, the elongated tubular member 150 is shown as being positioned in channels 160 of multiple pedicle screws 100*a* . . . 100*c*, where the pedicle screws 100*a* . . . 100*c* include pedicle screw heads 120*a* . . . 120*c* and pedicle screw shafts 140*a* . . . 140*c*, as shown in FIG. 1. Referring again to FIG. 2, in some embodiments, the compound includes polymethylmethacrylate (PMMA) or other suitable compound. Additional embodiments would include yet to be developed easily influenced liquids, semi-solid, solid compounds, or a combination thereof, that be converted into a rigid state in a fashion that can be implanted for the purposes of spinal instrumentation and fixation.

In another embodiment, the elongated spinal rod body 110 can represent a multi-segmented flexible and elongated rod that will be positioned in channels 160 of multiple pedicle screws 100*a* . . . 100*c*, where the pedicle screws 100*a* . . . 100*c* include pedicle screw heads 120*a* . . . 120*c* and pedicle screw shafts 140*a* . . . 140*c*. After capturing the rod within the pedicle screw head 160 with screw cap 130, the multi-segmented flexible rod will be made rigid by a collapsing process of the segments to a rigid construct.

In any spinal construct, the number of pedicle screw 100 segments fixed at an individual procedure is only limited by the surgical plan of the specialty surgeon and the anatomy of the patient. All embodiments detailed here can be used for fixation of any number of vertebral segments including fixation to the skull, sacrum and pelvis.

Figure 3:
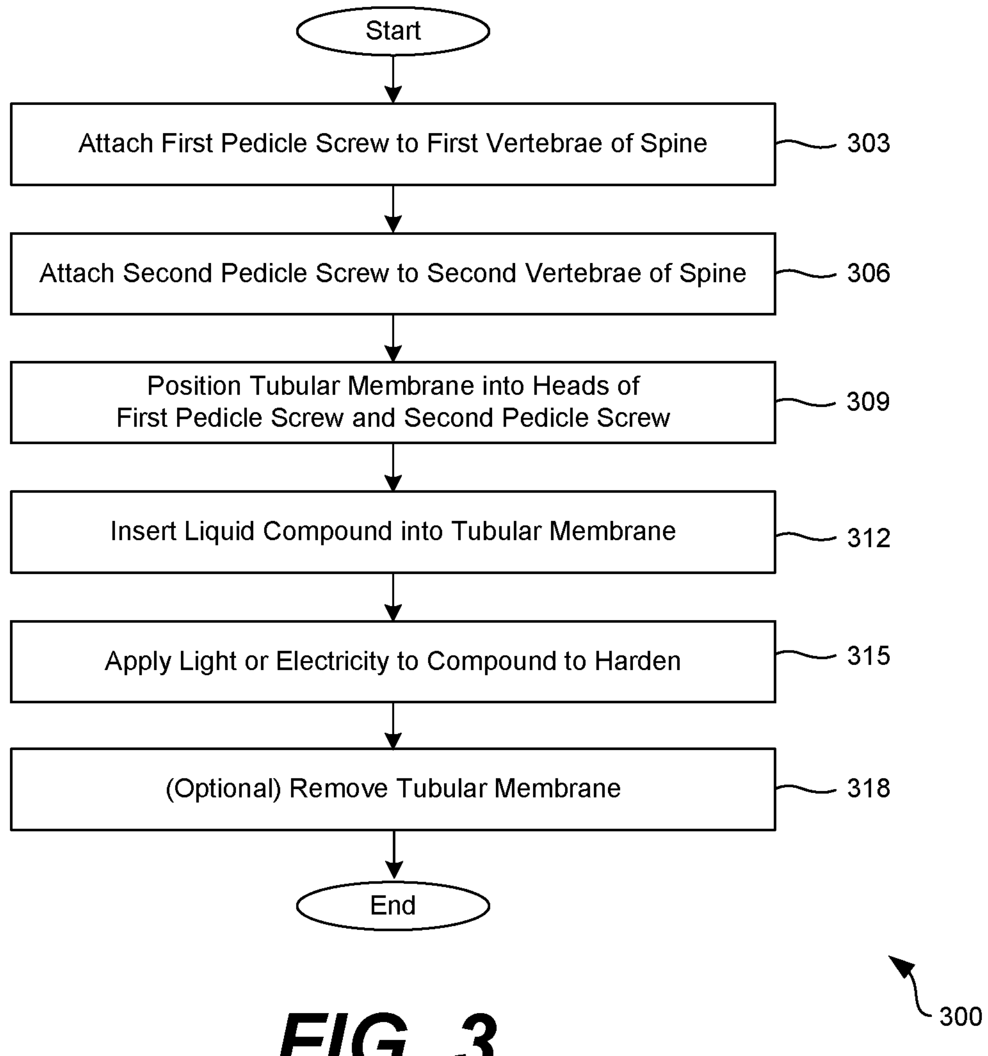
FIG. 3 shows a flowchart illustrating an example of the forming of a spinal rod member for use with the pedicle screws of FIGS. 1 and 2 according to various embodiments of the present disclosure.

Referring next to FIG. 3, a flowchart 300 is shown as an example of forming a spinal rod member 110 for use with one or more pedicle screws 100. Beginning with step 303, the method can include attaching a first pedicle screw 100*a* to a first vertebrae of a spine (not shown). Next, in step 306, the method can include attaching a second pedicle screw 100*b* to a second vertebrae of the spine (not shown). The first pedicle screw 100*a* and the second pedicle screw 100*b* can each include a pedicle screw head 120 and a pedicle screw shaft 140, as can be appreciated. Further, the pedicle screw head 120 of the first pedicle screw 100*a* and the second pedicle screw 100*b* can be configured to retain a spinal rod member 110 relative to the first pedicle screw 100*a* and the second pedicle screw 100*b*. In a similar fashion pedicle screw 100*b* can be configured to retain a spinal rod member 110 relative to a third pedicle screw 100*c* which will continue to retain a spinal rod member 110 relative to pedicle screw 100*d*.

Next, with respect to steps 309 to steps 318, the spinal rod member 110 can be formed. For instance, with respect to step 309, a flexible and elongated tubular membrane 150 can be positioned into the pedicle screw heads 120 of the first pedicle screw 100*a* and the second pedicle screw 100*b* (or other pedicle screws 100 as needed). Next, in step 312, a compound 180, such as a liquid, semi-solid or flexible solid compound configured to harden over time, can be inserted into the elongated tubular membrane 150. In step 315, the compound 180 can be hardened, for instance, to form a hardened spinal rod member body. In step 315, in some embodiments, changes in temperature, light or electricity that aid or achieves the hardening of the compound 180 can be applied. In step 318, the tubular membrane 150 can be optionally removed, although, in some embodiments, it is understood that the tubular membrane 150 can be left intact. Thereafter, the process can proceed to completion.

Disjunctive language such as the phrase “at least one of X, Y, or Z,” unless specifically stated otherwise, is otherwise understood with the context as used in general to present that an item, term, etc., can be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications can be made to the above-described embodiment(s) without departing substantially from the spirit and principles of the disclosure. All such modifications and variations are intended to be included herein within the scope of this disclosure and protected by the following claims and clauses.

Clause 1: A system, comprising: a pedicle screw comprising: a pedicle screw head; a pedicle screw shaft for implanting the pedicle screw in vertebra of a mammalian body; and a pedicle screw aperture, the pedicle screw aperture being configured to receive and retain the spinal rod member relative to the pedicle screw; and the spinal rod member, wherein the spinal rod member comprises: an elongated tubular membrane having a flexible body; and a spinal rod body formed inside the flexible body by a hardening of a compound, wherein the spinal rod body is formed by an insertion of a liquid, semi-solid, or flexible compound into the flexible body and converted into a solid body.

Clause 2. The clause of claim 1, wherein the hardening of the compound is performed by applying at least one of: a change in temperature of the compound, an application of light to the compound, an application of electricity to the compound, and an application of a hardening agent to the compound.

Clause 3. The system of any of clauses 1-2, wherein the compound comprises polymethylmethacrylate (PMMA).

Clause 4. The system of any of clauses 1-3, wherein the cross-section of the elongated tubular membrane is substantially similar to a cross-section of the screw head aperture that receives and retains the spinal rod member.

Clause 5. The system of any of clauses 1-4, wherein the spinal rod member has a substantially straight shape or a curvilinear shape.

Clause 6. A method, comprising: providing a pedicle screw, wherein the pedicle screw comprises: a pedicle screw head; a pedicle screw shaft for implanting the pedicle screw in vertebra of a mammalian body; and a pedicle screw aperture, the pedicle screw aperture being configured to receive and retain the spinal rod member relative to the pedicle screw; and providing the spinal rod member, wherein the spinal rod member comprises: an elongated tubular membrane having a flexible body; and a spinal rod body formed inside the flexible body by a hardening of a compound, wherein the spinal rod body is formed by an insertion of a liquid, semi-solid, or flexible compound into the flexible body and converted into a solid body.

Clause 7. The method of clause 6, wherein the compound comprises polymethylmethacrylate (PMMA).

Clause 8. The method of any of clauses 6-7, wherein the cross-section of the elongated tubular membrane is substantially similar to a cross-section of the screw head aperture that receives and retains the spinal rod member.

Clause 9. The method of any of claims 6-9, wherein the spinal rod member has a substantially straight shape or a curvilinear shape.

Clause 10. The method of any of clauses 6-10, further comprising: attaching the pedicle screw to a first vertebrae of the spine, the pedicle screw being a first pedicle screw; attaching a second pedicle screw to a second vertebrae of the spine, the second pedicle each comprising a second pedicle screw head and a second pedicle screw shaft, the second pedicle screw comprising a second aperture configured to retain a spinal rod member relative to the first pedicle screw and the second pedicle screw; and forming the spinal rod member by: positioning a flexible and elongated tubular membrane into the pedicle screw head of the first pedicle screw and the second pedicle screw; inserting a liquid compound into the elongated tubular membrane; and performing the hardening of the liquid compound to form a hardened spinal rod member body.

Clause 11. The method of any of clauses 6-10, wherein the hardening of the liquid compound is performed by applying at least one of: a change in temperature of the compound, an application of light to the compound, an application of electricity to the compound, and an application of a hardening agent to the compound.

Clause 12. A method, comprising: attaching a first pedicle screw to a first vertebrae of a spine; attaching a second pedicle screw to a second vertebrae of the spine, the first pedicle screw and the second pedicle screw each comprising a pedicle screw head and a pedicle screw shaft, the pedicle screw head being configured to retain a spinal rod member relative to the first pedicle screw and the second pedicle screw; forming the spinal rod member by: positioning a flexible and elongated tubular membrane into the pedicle screw head of the first pedicle screw and the second pedicle screw; inserting a liquid compound into the elongated tubular membrane; and hardening the liquid compound to form a hardened spinal rod member body, wherein the hardening of the liquid compound is performed by applying at least one of: a change in temperature of the compound, an application of light to the compound, an application of electricity to the compound, and an application of a hardening agent to the compound.

Clause 13. The method of clause 12, wherein the liquid compound comprises Polymethylmethacrylate (PMMA).

Clause 14. The method of any of clauses 12-13, wherein the cross-section of the elongated tubular membrane is substantially similar to a cross-section of a channel of the pedicle screw head of the first pedicle screw and the second pedicle screw configured to receive and retain the spinal rod member.

Clause 15. The method of any of clauses 12-14, wherein the spinal rod member can represent a multi-segmented flexible rod that is made rigid by a process of compression.

Therefore, the following is claimed:

1. A system, comprising:

a pedicle screw comprising:

a pedicle screw head;

a pedicle screw shaft for implanting the pedicle screw in vertebra of a mammalian body; and a pedicle screw aperture;

a coupling element attachable to the pedicle screw head; and a spinal rod member retained in the pedicle screw aperture and secured by the coupling element, wherein the spinal rod member comprises:

an elongated tubular membrane having a flexible body and a hollow interior; and a spinal rod body formed inside the flexible body by insertion of a compound into the flexible body that is converted into a solid body within the hollow interior through hardening of the compound, the elongated tubular membrane being formed of a material that provides structural resistance when the coupling element is attached to the pedicle screw head such that the spinal rod body is of a substantially uniform cross-section, and the elongated tubular membrane being removable from the spinal rod body after hardening of the compound.

2. The system of claim 1, wherein the hardening of the compound is performed by applying at least one of: a change in temperature of the compound, an application of light to the compound, an application of electricity to the compound, and an application of a hardening agent to the compound.

3. The system of claim 1, wherein the compound comprises polymethylmethacrylate (PMMA).

4. The system of claim 1, wherein a cross-section of the elongated tubular membrane is substantially similar to a cross-section of the pedicle screw aperture that receives and retains the spinal rod member.

5. The system of claim 1, wherein the spinal rod member has a substantially straight shape or a curvilinear shape.

6. The system of claim 1, wherein the coupling element is detachable from the pedicle screw head.

7. The system of claim 1, wherein the pedicle screw shaft comprises threaded elements for insertion into the vertebra.

8. A method, comprising:

providing a pedicle screw, wherein the pedicle screw comprises:

a pedicle screw head;

a pedicle screw shaft for implanting the pedicle screw in vertebra of a mammalian body;

a pedicle screw aperture; and a coupling element attachable to the pedicle screw head;

providing a spinal rod member that is retained in the pedicle screw aperture and secured by the coupling element, wherein the spinal rod member comprises:

an elongated tubular membrane having a flexible body and a hollow interior; and a spinal rod body detachable from the elongated tubular membrane and formed inside the flexible body within the hollow interior by an insertion of a compound into the flexible body that is converted into a solid body within the hollow interior through hardening of the compound, the elongated tubular membrane being formed of a material that provides structural resistance when the coupling element is attached to the pedicle screw head such that the spinal rod body is of a substantially uniform cross-section, and the elongated tubular membrane being removable from the spinal rod body after hardening of the compound.

9. The method of claim 8, wherein the compound comprises polymethylmethacrylate (PMMA).

10. The method of claim 8, wherein a cross-section of the elongated tubular membrane is substantially similar to a cross-section of the screw head aperture that receives and retains the spinal rod member.

11. The method of claim 8, wherein the spinal rod member has a substantially straight shape or a curvilinear shape.

12. The method of claim 8, further comprising:

attaching the pedicle screw to a first vertebrae of a spine, the pedicle screw being a first pedicle screw;

attaching a second pedicle screw to a second vertebrae of the spine, the first pedicle screw and the second pedicle screw each comprising a second pedicle screw head and a second pedicle screw shaft, the second pedicle screw comprising a second aperture configured to retain a spinal rod member relative to the first pedicle screw and the second pedicle screw; and forming the spinal rod member by:

positioning a flexible and elongated tubular membrane into the pedicle screw head of the first pedicle screw and the second pedicle screw;

attaching the coupling element to the pedicle screw head;

inserting a liquid compound into the elongated tubular membrane; and performing the hardening of the liquid compound to form a hardened spinal rod member body.

13. The method of claim 12, wherein the hardening of the liquid compound is performed by applying at least one of: a change in temperature of the compound, an application of light to the compound, an application of electricity to the compound, and an application of a hardening agent to the compound.

14. The method of claim 8, wherein the coupling element is detachable from the pedicle screw head.

15. A method, comprising:

attaching a first pedicle screw to a first vertebrae of a spine;

attaching a second pedicle screw to a second vertebrae of the spine, the first pedicle screw and the second pedicle screw each comprising a pedicle screw head, a coupling element attachable to the pedicle screw head, and a pedicle screw shaft, the coupling element being configured to secure the spinal rod member to the pedicle screw head; and forming a spinal rod member that is retained by the pedicle screw head by:

positioning a flexible and elongated tubular membrane into the pedicle screw head of the first pedicle screw and the second pedicle screw and attaching the coupling element to the pedicle screw head, the flexible and elongated tubular membrane having a hollow interior;

inserting a compound into the flexible and elongated tubular membrane within the hollow interior; and hardening the compound to form a hardened and rigid spinal rod member body, wherein the hardening of the compound is performed by applying at least one of: a change in temperature of the compound, an application of light to the compound, an application of electricity to the compound, and an application of a hardening agent to the compound, the elongated tubular membrane being formed of a material that provides structural resistance when the coupling element is attached to the pedicle screw head such that the spinal rod body is of a substantially uniform cross-section, and the elongated tubular membrane being removable from the spinal rod body after hardening of the compound.

16. The method of claim 15, wherein the compound comprises Polymethylmethacrylate (PMMA).

17. The method of claim 15, wherein the cross-section of the elongated tubular membrane is substantially similar to a cross-section of a channel of the pedicle screw head of the first pedicle screw and the second pedicle screw configured to receive and retain the spinal rod member.

18. The method of claim 15, wherein the coupling element is detachable from the pedicle screw head.

19. The method of claim 15, wherein the spinal rod member has a substantially straight shape or a curvilinear shape.

* * * * *